US012791640B2

(12) United States Patent
Qin et al.

(10) Patent No.: US 12,791,640 B2
(45) Date of Patent: Nov. 10, 2026

(54) WEARABLE RADIO FREQUENCY COIL ASSEMBLIES FOR MAGNETIC RESONANCE DEVICE

(71) Applicant: SHANGHAI UNITED IMAGING HEALTHCARE CO., LTD., Shanghai (CN)

(72) Inventors: Junjun Qin, Shanghai (CN); Pan Wu, Shanghai (CN); Shao Che, Shanghai (CN); Yanqi Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 6 days.

(21) Appl. No.: 18/957,842

(22) Filed: Nov. 24, 2024

(65) Prior Publication Data

US 2025/0298104 A1 Sep. 25, 2025

(30) Foreign Application Priority Data

Mar. 19, 2024 (CN) ......................... 202420536939.9
Mar. 28, 2024 (CN) ......................... 202420626077.9

(51) Int. Cl.
*G01R 33/34* (2006.01)
*A61B 5/055* (2006.01)

(52) U.S. Cl.
CPC ........ *G01R 33/34084* (2013.01); *A61B 5/055* (2013.01)

(58) Field of Classification Search
CPC .... G01R 33/34084; A61B 5/004; A61B 5/055
See application file for complete search history.

(56) References Cited

U.S. PATENT DOCUMENTS

2014/0005525 A1* 1/2014 Chen ................ G01R 33/34084 600/422
2023/0069540 A1* 3/2023 Wang ...................... H03F 3/195

* cited by examiner

*Primary Examiner* — Gerald Johnson
(74) *Attorney, Agent, or Firm* — METIS IP LLC

(57) ABSTRACT

A wearable radio frequency (RF) coil assembly for a magnetic resonance device is provided, including a plurality of malleable conductors forming a plurality of RF coils and a plurality of flexible cladding layers. At least two of the plurality of flexible cladding layers have an overlapping region, the overlapping region is capable of being adjusted, and the plurality of RF coils are disposed within the plurality of flexible cladding layers. Each of the plurality of flexible cladding layers is provided with a plurality of connecting components. The plurality of flexible cladding layers are connected to each other to enable the wearable RF coil assembly to form a wearable structure. The wearable structure adapts to detection sites of various sizes or shapes. When the wearable structure is worn by a detection object, an inner surface of the wearable structure adheres to a detection site of the detection object.

20 Claims, 17 Drawing Sheets

WEARABLE RADIO FREQUENCY COIL ASSEMBLIES FOR MAGNETIC RESONANCE DEVICE

CROSS-REFERENCE TO RELATED APPLICATIONS

This application claims priority to Chinese Patent Application No. 202420536939.9, filed on Mar. 19, 2024, and Chinese Patent Application 202420626077.9, filed on Mar. 28, 2024, the entire contents of each of which are hereby incorporated by reference.

TECHNICAL FIELD

The present disclosure relates to the field of magnetic resonance imaging technology, and in particular, to wearable radio frequency (RF) coil assemblies for magnetic resonance device.

BACKGROUND

Magnetic resonance imaging (MRI) is a technology widely used in medical imaging. The radio frequency (RF) coil is one of the main components of the magnetic resonance system and used to transmit the RF pulse to and/or receive a signal from a detection object. The RF coil is generally placed at a detection site of the detection object, and the better the fit between the RF coil and the detection site, the higher the image quality. However, in actual clinical scanning, due to the differences in the structure and size of the detection site of different detection objects, there is usually a gap between the RF coil and the detection site, resulting in poor scanning and imaging results of the magnetic resonance system.

Therefore, it is desired to provide wearable RF coil assemblies for a magnetic resonance device to improve the scanning imaging effect of the magnetic resonance system.

SUMMARY

One embodiment of the present disclosure provides a wearable radio frequency (RF) coil assembly for a magnetic resonance device. The wearable RF coil assembly may include a plurality of malleable conductor forming a plurality of RF coils of the magnetic resonance device and a plurality of flexible cladding layers. At least two of the plurality of flexible cladding layers may have an overlapping region, the overlapping region may be capable of being adjusted, and the plurality of RF coils may be disposed within the plurality of flexible cladding layers. Each of the plurality of flexible cladding layers may be provided with a plurality of connecting components. The plurality of flexible cladding layers may be connected to each other by the plurality of connecting components to enable the wearable RF coil assembly to form a wearable structure. The wearable structure may adapt to detection sites of various sizes or shapes, and when the wearable structure is worn by a detection object, an inner surface of the wearable structure may adhere to a detection site of the detection object.

In some embodiments, when the wearable structure is worn, the wearable structure may be in a shape of a tube, a helmet, a boot, or a scapula.

In some embodiments, when the wearable structure is worn, the wearable structure may be in the shape of the scapular, the detection site may be a shoulder, and the plurality of flexible cladding layers may include a first layer and two second layers. The two second layers may be respectively provided on a left side and a right side of the first layer, and partially overlap with the first layer respectively. When the plurality of flexible cladding layers wrap the shoulder, the two second layers may be capable of being moved relative to the first layer to allow a detection space of the wearable structure to adapt to the shoulder.

In some embodiments, the plurality of connecting components may include a first connecting mechanism. One end of the first connecting mechanism may be connected to one of the two second layers and the other end of the first connecting mechanism may be connected to the other of the two second layers or the first layer.

In some embodiments, the plurality of connecting components may further include a second connecting mechanism. One end of the second connecting mechanism may be connected to one of the two second layers and the other end of the second connecting mechanism may be connected to the other of the two second layers, and the second connecting mechanism may be configured to be fitted onto the detection object and tension the two second layers.

In some embodiments, the first layer may include a first portion and a second portion. The two second layers and the second portion may be connected to the first portion, the two second layers may be respectively located on two sides of the first portion and partially overlap with the second portion respectively, the two second layers may be capable of being moved relative to the second portion.

In some embodiments, the plurality of connecting components may further include a third connecting mechanism. Two ends of the third connecting mechanism may be respectively connected to two opposite ends of the first portion, the third connecting mechanism and the first portion may enclose a hole for an upper arm of the detection object to pass through, and a length of the third connecting mechanism may be capable of being adjusted.

In some embodiments, a region, disposed between the two second layers, of the first layer may have an arcuate notch for avoiding a neck of the detection object.

In some embodiments, when the wearable structure is worn, the wearable structure may be in the shape of the tube, the plurality of connecting components may be provided along a circumferential direction of the plurality of flexible cladding layers, the plurality of connecting components may include a first connecting unit and a second connecting unit, and the first connecting unit may be capable of being detachably connected to different positions of the second connecting unit to adjust a circumferential dimension of a detection space enclosed by the plurality of flexible cladding layers along the circumferential direction of the plurality of flexible cladding layers.

In some embodiments, the first connecting unit may include a first connecting sub-portion and the second connecting unit may include a first connecting mother portion. The plurality of flexible cladding layers may include a main layer and an accessory layer, the first connecting sub-portion may be disposed on the main layer, the first connecting mother portion may be disposed on the accessory layer, and the first connecting sub-portion may be capable of being detachably connected to different positions of the first connecting mother portion.

In some embodiments, the main layer and the accessory layer may have an overlapping region and the accessory layer may be capable of being connected to different positions of the main layer to adjust an area of the overlapping region. The accessory layer may be capable of being moved in the circumferential direction to enable an end of the accessory layer along a direction perpendicular to the circumferential direction to be capable of being detachably connected to the different positions of the main layer, or the first connecting mother portion may be provided at the end of the accessory layer along the circumferential direction, and the other end of the accessory layer along the circumferential direction may be fixedly connected to the main layer.

In some embodiments, the accessory layer may be convex in a direction away from the plurality of RF coils, and the main layer may be concave in a direction away from the plurality of RF coils.

In some embodiments, the first connecting unit may include a second connecting sub-portion and the second connecting unit may include a second connecting mother portion. The main layer may include a first sub-layer and a second sub-layer connected to each other and distributed in a direction perpendicular to the circumferential direction, the first connecting sub-portion may be disposed in the second sub-layer, the second connecting sub-portion and the second connecting mother portion may be respectively disposed at two ends of the first sub-layer along the circumferential direction, and the second connecting sub-portion may be capable of being detachably connected to different positions of the second connecting mother portion.

In some embodiments, the first connecting unit may include a third connecting sub-portion spaced from the second connecting sub-portion, and the second connecting unit may include a third connecting mother portion spaced from the second connecting mother portion. The main layer may further include a third sub-layer distributed in the direction perpendicular to the circumferential direction and connected to the second sub-layer, the third connecting sub-portion and the third connecting mother portion may be respectively disposed at two ends of the third sub-layer along the circumferential direction, the third connecting sub-portion may be capable of being detachably connected to different positions of the third connecting mother portion, and a dimension of the third sub-layer along the circumferential direction may be smaller than a dimension of the first sub-layer along the circumferential direction.

In some embodiments, an interior of at least one of the plurality of flexible cladding layers may be a sandbag structure, the sandbag structure may include at least two partitions, neighboring partitions of the at least two partitions may be divided by sutures, and each of the at least two partitions may be filled with a filler.

In some embodiments, the wearable RF coil assembly may further include an amplifier connected to the plurality of the RF coils by a wired connection or a wireless connection.

One embodiment of the present disclosure provides a wearable RF coil assembly for a magnetic resonance device. The wearable RF coil assembly may include a plurality of malleable conductors forming a plurality of RF coils of the magnetic resonance device and a wearable structure. The wearable structure may include an upper arm portion and a shoulder portion connected with each other, both the upper arm portion and the shoulder portion may include flexible cladding layers provided with the plurality of RF coils, the upper arm portion may surround an upper arm of a detection object, the shoulder portion may wrap around front and back of a shoulder of the detection object, the flexible cladding layers may include at least two layers, and the at least two layers may be capable of being moved relative to each other to allow a detection space of the wearable structure to be adapted to the shoulder of the detection object.

In some embodiments, the flexible cladding layers of the wearable structure may include three layers, two layers of the three layers may be respectively disposed on a left side and a right side of the other layer of the three layers and have an overlapping region with the other layer respectively. When the wearable structure wraps the shoulder of the detection object, the three layers may be capable of being moved relative to each other to enable the detection space of the wearable structure to be adapted to the shoulder of the detection object.

One embodiment of the present disclosure provides a wearable RF coil assembly for a magnetic resonance device. The wearable RF coil assembly may include a plurality of malleable conductors forming a plurality of RF coils of the magnetic resonance device and a wearable structure. The wearable structure may include a main portion and an accessory portion connected with each other. Both the main portion and the accessory portion may include flexible cladding layers provided with the plurality of RF coils, the main portion and the accessory portion may have an overlapping region, and the accessory portion may be connected to different positions of the main portion by a detachable structure to adjust an area of the overlapping region.

In some embodiments, the main portion may include a first sub-layer, a second sub-layer, and a third sub-layer distributed in a direction perpendicular to a circumferential direction of the flexible cladding layers. The first sub-layer and the third sub-layer may be connected to the second sub-layer, and a dimension of the third sub-layer along the circumferential direction may be smaller than a dimension of the first sub-layer along the circumferential direction.

Additional features may be set forth in part in the description which follows, and in part may become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
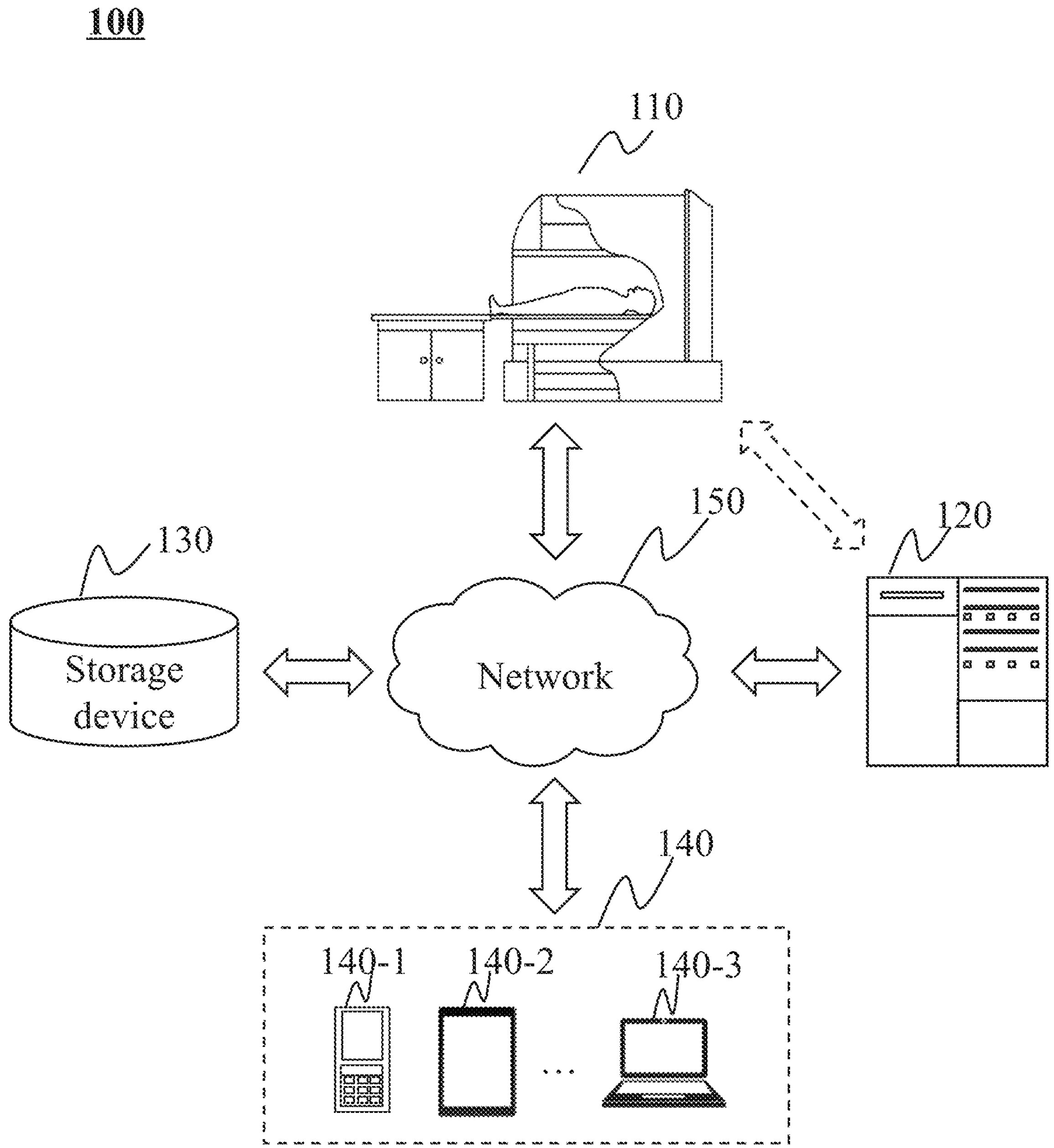
FIG. 1 is a schematic diagram illustrating an exemplary medical imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in the present disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by other expressions if they may achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any or all combinations of one or more of the associated listed items.

These and other features, and characteristics of the present disclosure, as well as the methods of operation and functions of the related elements of structure and the combination of parts and economics of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Radio frequency (RF) coil assemblies used in a magnetic resonance system are categorized into a rigid coil assembly and a flexible coil assembly based on differences in material composition.

Figure 2A:
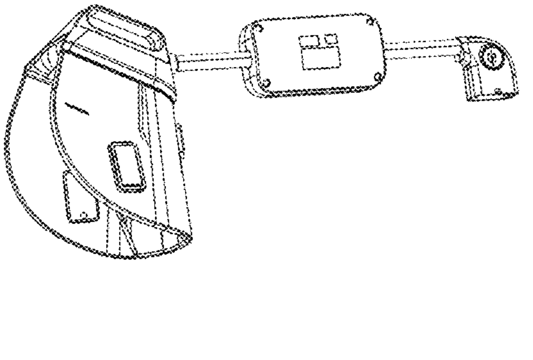
FIG. 2A and FIG. 2B are schematic diagrams illustrating exemplary magnetic resonance RF coil assemblies according to some embodiments of the present disclosure.
Figure 2B:
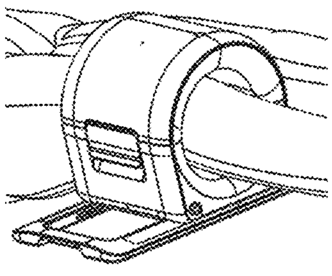

The rigid coil assembly is made of rigid plastic, with RF coils attached inside the plastic housing. In order to accommodate different detection objects (e.g., patients), the housing of the rigid coil assembly is designed to be relatively large. However, when a detection site with a small size of the detection object wears the rigid coil assembly, there is a large distance between the detection site and RF coils in the rigid coil assembly, which results in poor scanning imaging of the magnetic resonance system. For example, FIG. 2A and FIG. 2B are schematic diagrams illustrating exemplary magnetic resonance RF coil assemblies according to some embodiments of the present disclosure. FIG. 2A illustrates a rigid coil assembly of the shoulder joint and FIG. 2B illustrates a rigid coil assembly of the knee joint. As can be seen in FIGS. 2A and 2B, for some detection objects (e.g., thinner patients), the inner surface of the rigid coil assembly fits poorly to the detection site of the detection object.

Figure 3:
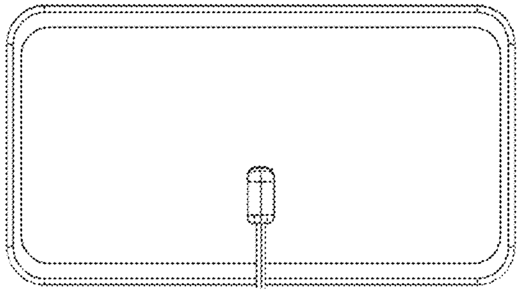
FIG. 3 is a schematic diagram illustrating an exemplary magnetic resonance RF coil assembly according to some embodiments of the present disclosure.

The flexible coil assembly may be bent. However, the flexible coil assembly is usually of a planar-type design, which may only wrap around the maximum size of the joint after bending, making it difficult to fit perfectly with the detection site of the detection object, and thus affecting the quality of the scanning imaging of the magnetic resonance system. For example, FIG. 3 is a schematic diagram illustrating an exemplary magnetic resonance RF coil assembly according to some embodiments of the present disclosure. FIG. 3 illustrates a flexible universal coil assembly. As can be seen in FIG. 3, although the flexible coil assembly may be applied to different body parts, it is difficult to completely fit with the detection site of the detection object.

In addition, the RF coil assembly of the current magnetic resonance system can only be used on a magnetic resonance scanning bed. In the process of use, the RF coil assembly is set up first, the cable of the RF coil assembly is connected to the scanning bed of the magnetic resonance system, and then the center of the detection site of the detection object is set close to the center of the RF coil assembly, and finally, the RF coil assembly is closed. This process is complicated, takes a long time, and requires a high degree of cooperation with the detection object.

The present disclosure provides a wearable RF coil assembly for a magnetic resonance device. The wearable RF coil assembly includes a plurality of malleable conductors and a plurality of flexible cladding layers. The plurality of malleable conductors form a plurality of RF coils of the magnetic resonance device. At least two of the plurality of flexible cladding layers have an overlapping region, and the overlapping region is capable of being adjusted. The plurality of RF coils are disposed within the plurality of flexible cladding layers. Each of the plurality of flexible cladding layers is provided with a plurality of connecting components. The plurality of flexible cladding layers are connected to each other by the plurality of connecting components to enable the wearable RF coil assembly to form a wearable structure. The wearable structure adapts to detection sites of various sizes or shapes. When the wearable structure is worn by the detection object, an inner surface of the wearable structure adheres to the detection site of the detection object.

According to the embodiments of the present disclosure, the RF coil assembly of the magnetic resonance system may be configured to form a wearable structure, which is capable of adapting to detection sites of various sizes or shapes, so as to enable the RF coil in the RF coil assembly to be closely adhered to the detection site of the detection object, thereby improving the quality of scanning imaging. At the same time, the detection object can wear the RF coil assembly to the relevant detection site by himself/herself outside the scanning room of the magnetic resonance system, and after entering the scanning room, the detection object only needs to lie down on the scanning bed of the magnetic resonance system and connect the RF coil assembly to the magnetic resonance device, which greatly reduces the complexity of the workflow, saves time, and greatly reduces the requirement for the cooperation of the detection object, thus improving the scanning efficiency.

FIG. 1 is a schematic diagram illustrating an exemplary medical imaging system 100 according to some embodiments of the present disclosure. As shown in FIG. 1, the medical imaging system 100 may include an imaging device 110, a processing device 120, a storage device 130, one or more terminals 140, and a network 150. In some embodiments, the imaging device 110, the processing device 120, the storage device 130, and/or the terminal(s) 140 may be connected to and/or communicate with each other via a wireless connection, a wired connection, or a combination thereof.

The imaging device 110 may be configured to scan a detection object (or a part of the subject) to acquire medical image data associated with the detection object. The medial image data relating to the detection object may be used for generating a medical image (e.g., an MR image) of the detection object. The medical image may illustrate an internal structure and the health condition of the detection object. In some embodiments, the imaging device 110 may include an imaging device based on the magnetic resonance technology, which may be a single-modality scanner and/or multi-modality scanner. The single modality scanner may include, for example, a magnetic resonance imaging (MRI) scanner, or the like. The multi-modality scanner may include, for example, a single-photon emission computed tomography-magnetic resonance imaging (SPECT-MRI) scanner, an X-ray imaging-magnetic resonance imaging (X-ray-MRI) scanner, etc. It should be noted that the imaging device 110 described below is merely provided for illustration purposes, and not intended to limit the scope of the present disclosure.

In some embodiments, the imaging device 110 may include an RF coil assembly for transmitting an RF pulse and/or receiving a signal. In some embodiments, the RF coil assembly may be wearable. The wearable RF coil assembly includes a plurality of malleable conductors and a plurality of flexible cladding layers. The plurality of malleable conductors form a plurality of RF coils of the magnetic resonance device. At least two of the plurality of flexible cladding layers have an overlapping region, and the overlapping region is capable of being adjusted. The plurality of RF coils are disposed within the plurality of flexible cladding layers. Each of the plurality of flexible cladding layers is provided with a plurality of connecting components. The plurality of flexible cladding layers are connected to each other by the plurality of connecting components to enable the wearable RF coil assembly to form a wearable structure. The wearable structure can adapt to detection sites of various sizes or shapes, and an inner surface of the wearable structure can adhere to the detection site of the detection object when the wearable structure is worn by the detection object.

In some embodiments, the processing device 120 may be a single server or a server group. The server group may be centralized or distributed. The processing device 120 may process data and/or information obtained from the imaging device 110, the storage device 130, and/or the terminal(s) 140. For example, the processing device 120 may generate a medical image of the detection object based on scan data acquired in a medical scan of the detection object. In some embodiments, the processing device 120 may be local or remote from the medical imaging system 100. In some embodiments, the processing device 120 may be implemented on a cloud platform. In some embodiments, the processing device 120 or a portion of the processing device 120 may be integrated into the imaging device 110 and/or the terminal(s) 140.

The storage device 130 may store data, instructions, and/or any other information. In some embodiments, the storage device 130 may store data obtained from the imaging device 110, the processing device 120, and/or the terminal(s) 140. In some embodiments, the storage device 130 may store data and/or instructions that the processing device 120 may execute or use. In some embodiments, the storage device 130 may include a mass storage device, a removable storage device, a volatile read-and-write memory, a read-only memory (ROM), or the like, or a combination thereof. In some embodiments, the storage device 130 may be implemented on a cloud platform. In some embodiments, the storage device 130 may be part of the imaging device 110, the processing device 120, and/or the terminal(s) 140.

The terminal(s) 140 may be configured to enable a user interaction between a user and the medical imaging system 100. In some embodiments, the terminal(s) 140 may be connected to and/or communicate with the imaging device 110, the processing device 120, and/or the storage device 130. In some embodiments, the terminal(s) 140 may include a mobile device 140-1, a tablet computer 140-2, a laptop computer 140-3, or the like, or a combination thereof. In some embodiments, the terminal(s) 140 may be part of the processing device 120 and/or the imaging device 110.

The network 150 may include any suitable network that can facilitate the exchange of information and/or data for the medical imaging system 100. In some embodiments, one or more components of the medical imaging system 100 (e.g., the imaging device 110, the processing device 120, the storage device 130, the terminal(s) 140, etc. may communicate information and/or data with one or more other components of the medical imaging system 100 via the network 150.

It should be noted that the above description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the medical imaging system 100 may include one or more additional components and/or one or more components described above may be omitted. Additionally or alternatively, two or more components of the medical imaging system 100 may be integrated into a single component. However, those variations and modifications do not depart from the scope of the present disclosure.

Figure 4:
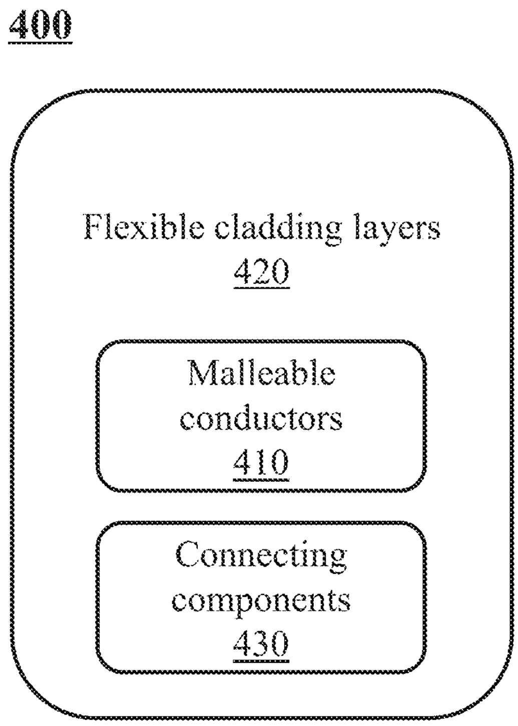
FIG. 4 is a schematic diagram illustrating an exemplary wearable RF coil assembly according to some embodiments of the present disclosure.

FIG. 4 is a schematic diagram illustrating an exemplary wearable RF coil assembly according to some embodiments of the present disclosure. As shown in FIG. 4, the wearable RF coil assembly 400 includes a plurality of malleable conductors 410 and a plurality of flexible cladding layers 420. The plurality of malleable conductors 410 may be flexible, and enable complex and irregular surface contours.

The plurality of malleable conductors 410 may form a plurality of RF coils of a magnetic resonance device (e.g., the imaging device 110). In some embodiments, the malleable conductors 410 include malleable conductors 800 in FIG. 8 or malleable conductors 1000 in FIG. 10.

At least two of the plurality of flexible cladding layers 420 have an overlapping region. An area of the overlapping region may be adjusted. The plurality of RF coils may be disposed within the plurality of flexible cladding layers 420.

In some embodiments, the area of the overlapping region of the different flexible cladding layers is determined by a machine learning model. An input of the machine learning model is information about the detection object (e.g., age, gender, height, weight, etc.), the detection site of the detection object, etc., and an output of the machine learning model is the area of the overlapping region or a range of the area.

In some embodiments, a size of the overlapping region of the flexible cladding layers is positively correlated with a diameter of the RF coils in the flexible cladding layers. For example, the larger the diameter of the RF coils in the flexible cladding layers, the larger the size of the overlapping region of the flexible cladding layers.

Each of the plurality of flexible cladding layers 420 is provided with a plurality of connecting components 430. The plurality of flexible cladding layers 420 are connected to each other via the plurality of connecting components 430 to enable the wearable RF coil assembly 400 to form a wearable structure. The wearable structure can adapt to detection sites of various sizes or shapes (e.g., shoulders, elbows, knees, heads, feet, etc., of different patients), and an inner surface of the wearable structure can adhere to the detection site of the detection object when the wearable structure is worn by the detection object. In some embodiments, the flexible cladding layers 420 include flexible cladding layers 500 in FIG. 5 or flexible cladding layers 900 in FIG. 9.

According to the embodiments of the present disclosure, connecting the plurality of flexible cladding layers 420 by the connecting components 430 causes the RF coil assembly 400 to form the wearable structure that is capable of adapting to the detection sites of various sizes or shapes and highly adhering to the detection site, thereby improving the quality of the magnetic resonance imaging. Additionally, in clinical usage, the detection object only needs to wear the wearable structure to the appropriate detection site, enter the scanning room of the magnetic resonance device, lie on the scanning bed of the magnetic resonance device, and connect the RF coil assembly to the magnetic resonance device, which greatly reduces the complexity of the workflow, saves time, and requires much less cooperation from the detection object, thereby improving scanning efficiency.

In some embodiments, when the wearable structure formed by the wearable RF coil assembly 400 is worn, the wearable structure is in a shape of a tube, a helmet, a boot, or a scapula, etc. When the wearable structure is in the shape of a tube when worn, it may apply to a detection site that is substantially cylindrical in shape, for example, the knee, elbow, or the chest, etc. When the wearable structure is in the shape of a helmet when worn, it may apply to a detection site that is substantially spherical in shape, for example, the head, etc. When the wearable structure is in the shape of a boot when worn, it may apply to a detection site such as a foot. When the wearable structure is the shape of a scapular when worn, it may apply to a detection site such as the shoulder or the chest. With a plurality of shapes of the wearable structures, different types of detection sites may be adapted, which improves the adaptability and wearability flexibility of the RF coil assembly and improves scanning efficiency.

It should be noted that the above descriptions of the wearable RF coil assembly 400 are provided for the purposes of illustration, and are not intended to limit the scope of the present disclosure. For persons having ordinary skills in the art, various modifications and changes in the forms and details of the application of the above system may occur without departing from the principles of the present disclosure. In some embodiments, the wearable RF coil assembly 400 may include one or more other components and/or one or more components described above may be omitted. However, those variations and modifications also fall within the present disclosure.

In some embodiments, when a wearable structure formed by the wearable RF coil assembly (e.g., the wearable RF coil assembly 400) is worn, the wearable structure is in the shape of a scapular, the detection site is the shoulder. The following takes the wearable RF coil assembly shown in FIG. 5-FIG. 8 as an example to describe the scapular-shaped wearable RF coil assembly. The wearable RF coil assembly illustrated in FIG. 5-FIG. 8 may include flexible cladding layers 500 and malleable conductors 800.

Figure 5:
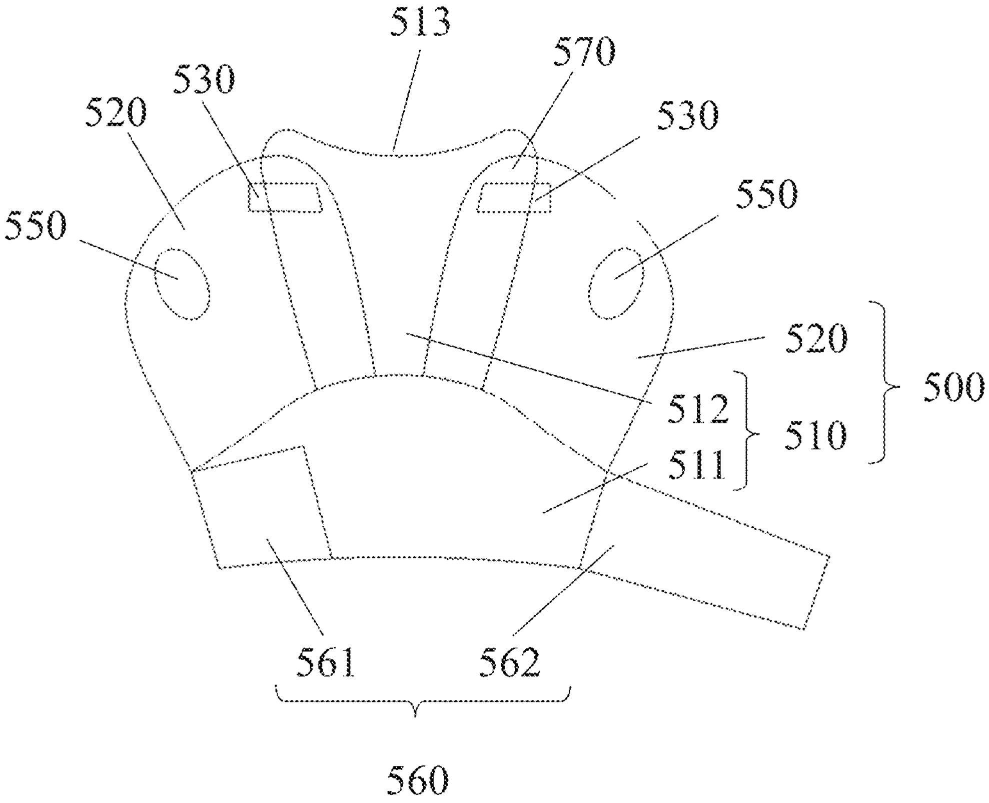
FIG. 5 is a schematic diagram illustrating an exemplary wearable RF coil assembly when unfolded according to some embodiments of the present disclosure.
Figure 6:
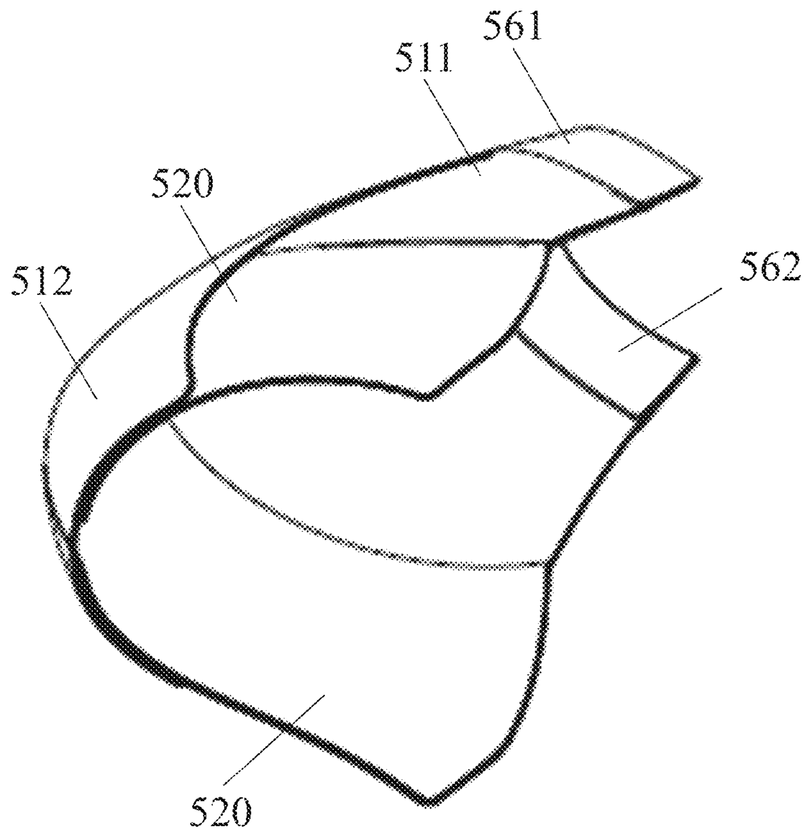
FIG. 6 is a schematic diagram illustrating an exemplary wearable structure formed by the wearable RF coil assembly in FIG. 5.
Figure 7:
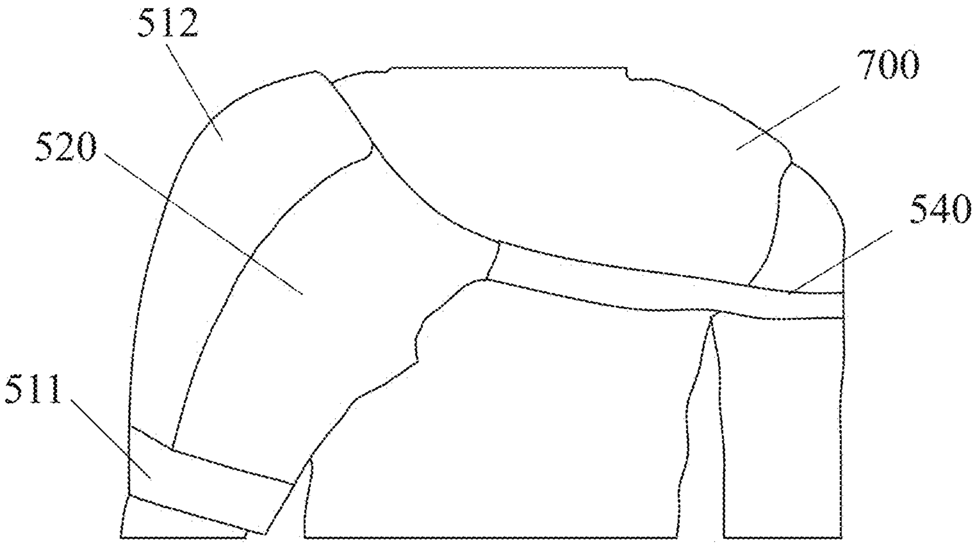
FIG. 7 is a schematic diagram illustrating that a detection object wears the wearable RF coil assembly in FIG. 5.
Figure 8:
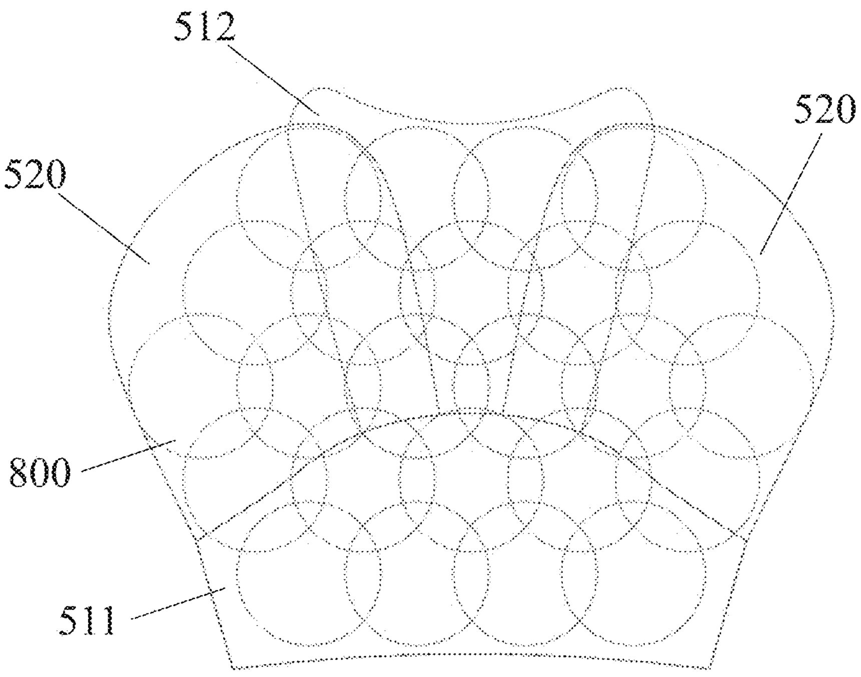
FIG. 8 is a schematic diagram illustrating RF coils in the wearable RF coil assembly in FIG. 5.

FIG. 5 is a schematic diagram illustrating an exemplary wearable RF coil assembly when unfolded according to some embodiments of the present disclosure. FIG. 6 is a schematic diagram illustrating an exemplary wearable structure formed by the wearable RF coil assembly in FIG. 5. FIG. 7 is a schematic diagram illustrating that a detection object wears the wearable RF coil assembly in FIG. 5. FIG. 8 is a schematic diagram illustrating RF coils in the wearable RF coil assembly in FIG. 5. The flexible cladding layers 500 of the wearable RF coil assembly may be encapsulated by a flexible material such as felt, polyurethane (PU) material, etc., using hot pressing or sewing processes, which have a certain flexibility and may be bent to a certain extent. The wearable RF coil assembly includes a plurality of flexible cladding layers 500. For example, as shown in FIG. 5, the flexible cladding layers 500 of the wearable RF coil assembly include a first layer 510 and two second layers 520. As shown in FIG. 6, a wearable structure formed by the wearable RF coil assembly in FIG. 5 is in the shape of a scapular when worn, in such cases, the detection site is the shoulder (as shown in FIG. 7). As shown in FIG. 8, a plurality of RF coils formed by the malleable conductors 800 are provided within the flexible cladding layers 500.

In some embodiments, the two second layers 520 are respectively provided on a left side and a right side of the first layer 510, and partially overlap with the first layer 510 respectively. When the flexible wrapping layers 500 wrap the shoulder, the two second layers 520 may be capable of being moved relative to the first layer 510 to allow a detection space of the wearable structure to adapt to the shoulder. In some embodiments, the two second layers 520 are the same such that the RF coil assembly can adapt to fit both the left and right shoulders.

As shown in FIG. 7, the first layer 510 is configured to be affixed to the acromion region of the shoulder and the upper arm region of the detection object 700, so that the relative positions of the wearable structure and the detection object 700 are fixed, and the two second layers 520 are configured to be affixed respectively to the chest region and the scapular region of the shoulder of the object 700, respectively. By the movement of any one second layer 520 relative to the first layer 510, the area of an overlapping region 570 of the second layer 520 and the first layer 510 may be changed, thereby changing the size, covered by the second layer 520, of the chest region or the scapular region of the shoulder of the detection object 700 and a position of the second layers 520 relative to the first layer 510, so as to adapt to the detection object 700 with different body shapes or different shoulder thicknesses, to highly fit with the shoulder of the detection object 300.

The first layer 510 and the two second layers 520 are provided with malleable conductors 800, so that both the first layer 510 and the second layers 520 include RF coils (RF coils formed by the malleable conductors 800). The malleable conductors can deform, thereby facilitating adaptation to the shoulder of the detection object. During the magnetic resonance imaging process, a better fit to the shoulder of the detection object is achieved by the flexible cladding layers of the wearable RF coil assembly, thereby improving the quality of the acquired scanning image.

As shown in FIG. 7, the detection object 700 can wear the wearable RF coil assembly shown in FIG. 5 to the shoulder by himself/herself. After entering the scanning room of the magnetic resonance device, the detection object 700 only needs to lie down on the scanning bed of the magnetic resonance device, which does not require an operator (e.g., a doctor) to lay out the RF coil assembly in advance and to have the shoulder of the detection object 700 go to converge on the center of the RF coil assembly, thus greatly reducing workflow complexity, saving time, and increasing scanning efficiency.

In some embodiments, as shown in FIG. 5, the plurality of connecting components in the wearable RF coil assembly include a first connecting mechanism 530. One end of the first connecting mechanism 530 is connected to one of the two second layers 520, and the other end of the first connecting mechanism 530 is connected to the other of the two second layers 520 or the first layer 510. The length of the first connecting mechanism 530 may be adjusted to change the area of the overlapping region 570 between a corresponding second layer 520 and the first layer 510.

Specifically, the first connecting mechanism 530 may be provided such that the corresponding second layer 520 may be moved with respect to the first layer 510 to change the area of the overlapping region 570. Additionally, the first connecting mechanism 530 may serve as a limiting function to ensure that the corresponding second layer 520 is stably adhered to the chest region or the scapular region of the shoulder of the detection object 700.

Further, the number of the first connecting mechanism 530 may be two, and each of the two second layers 520 is connected to the first layer 510 via one of the first connecting mechanisms 530. In some embodiments, the number of first connecting mechanism 530 may be more than two, e.g., three, four, etc.

Furthermore, one end of the first connecting mechanism 530 is connected to an edge region of the second layers 520 proximate to the first layer 510, and the other end of the first connecting mechanism 530 is connected to an edge region of the first layer 510 proximate to the second layers 520.

In some embodiments, one end of the first connecting mechanism 530 is connected to one of the two second layers 520, and the other end of the first connecting mechanism 530 is connected to the other of the two second layers 520. The first connecting mechanism 530 may change its length by telescoping to change a distance between the two second layers 520, and thus a distance between each of the second layer 520 and the first layer 510. By connecting the first connecting mechanism 530 to ends of the two second layers 520 close to each other, a tensile force toward the first layer 510 is ensured to be exerted on each of the second layers 520, such that each second layer 520 partially overlap with the first layer 510, the wearable RF coil assembly of the shoulder is not easily loosened when being worn, and the wearing stability is improved.

In some embodiments, as shown in FIG. 7, the plurality of connecting components in the wearable RF coil assembly include a second connecting mechanism 540. One end of the second connection mechanism 540 is connected to one of the two second layers 520 and the other end of the second connection mechanism 540 is connected to the other of the two second layers 520. The second connecting mechanism 530 is configured to snap onto the detection object 700 and tension the two second layers 520.

Specifically, the first connecting mechanism 530 is configured to tension the ends of the two second layers 520 close to each other, and the second connecting mechanism 540 is configured to tension the ends of the two second layers 520 far away from each other, so that the two second layers 520 may be stably confined to the detection object 700 to maintain a stable fit with the chest region or the scapular region of the shoulder of the detection object 700, which further improves the stability of the wearable RF coil assembly of the shoulder when worn.

Further, the second connecting mechanism 540 may adjust its length by telescoping, thereby adapting to more different body sizes of the detection object 700 without changing the area of the overlapping regions 570 between the second layers 520 and the first layer 510, further improving the adaptability of the wearable RF coil assembly of the shoulder when worn. Preferably, the second connecting mechanism 540 may be an elastic strap. The second connecting mechanism 540 may pass from the front chest of the detection object 700 through the armpit of the non-scanning side of the detection object 700 (as shown in FIG. 7), or the second connecting mechanism 540 may bypass the neck of the detection object 700.

In some embodiments, as shown in FIG. 5, the first layer 510 may include a first portion 511 and a second portion 512. The two second layers 520 and the second portion 512 are connected to the first portion 511. The two second layers 520 are connected to the second portion 512 via the first connecting mechanism 530. The two second layers 520 are respectively located on two sides of the first portion 511 and partially overlap with the second portion 512, respectively. Each second layer 520 is capable of being moved relative to the second portion 512 to change the area of the corresponding overlapping region 570.

Specifically, as shown in FIG. 7, the first portion 511 is configured to be affixed to the upper arm region of the shoulder of the detection object 700, and the second portion 512 is configured to be affixed to the acromion region of the shoulder of the detection object 700. There is a large difference in the shoulder thicknesses of detection objects 700 of different body shapes. By connecting the second layers 520 to the second portion 512 via the first connecting mechanism 530, the position of the second layers 520 may be conveniently adjusted, thus the second layers 520 are made to fit closely with the chest region or the scapular region of the shoulders of the detection objects 700 with different shoulder thicknesses.

In some embodiments, the second layers 520 are connected to the first portion 511 via the first connecting mechanism 530, or the second layers 520 are connected to the first portion 511 and the second portion 512 respectively via the first connecting mechanism 530.

In some embodiments, as shown in FIG. 5, the plurality of connecting components in the wearable RF coil assembly include a third connecting mechanism 560. Two ends of the third connecting mechanism 560 are respectively connected to two opposite ends of the first portion 511. The third connecting mechanism 560 and the first portion 511 enclose a hole (referred to as a wearing hole) for the upper arm of the detection object 700 to pass through, and the length of the third connecting mechanism 560 may be adjusted. Preferably, the third connecting mechanism 560 is an elastic strap.

Specifically, the length of the third connecting mechanism 560 may be adjusted by expansion and contraction so as to adjust the size of the wearing hole. Thus, the first portion 511 is fixedly snapped onto the upper arm of the detection object 700, and the wearable structure may be relatively fixed to the shoulder of the detection object 700. At the same time, the wearable structure can adapt to the detection object 700 with different arm thicknesses, which improves the stability and adaptability of the shoulder wearable RF coil assembly when worn.

In some embodiments, at least one of the first connecting mechanism 530, the first connecting mechanism 540, or the third connecting mechanism 560 may be a detachable structure. The detachable structure includes one of Velcro, a snap-on structure, a belt-like structure, or a tieable cord structure, or any combination thereof. With the detachable structure, the length of the connecting structure (e.g., the first connecting mechanism 530, the first connecting mechanism 540, the third connecting mechanism 560) can be varied to adapt to the dimensions of the shoulder of the detection object 700, so as to make the RF coil assembly fit the shoulder more closely, and at the same time improve the wearing convenience of the RF coil assembly.

For example, the second connecting mechanism 540 and at least one of the two second layers 520 may be detachably connected, thereby facilitating the second connecting mechanism 540 to be worn on the detection object 700 to facilitate the detection object 700 to wear the RF coil assembly. In some embodiments, the second connecting mechanism 540 may be bonded to at least one of the two second layers 520. In some embodiments, ends of the two second layers 520 that are away from each other are provided with Velcroes 550, and the Velcroes 550 are provided for bonding with the second connecting mechanism 540.

As another example, as shown in FIG. 5, the third connecting mechanism 560 may include a first connecting strap 561 and a second connecting strap 562. The first connecting strap 561 and the second connecting strap 562 are connected to the two ends of the first portion 511, respectively. When the first connecting strap 561 is connected to the second connecting strap 562, the first connecting strap 561 and the second connecting strap 562 may enclose a wearing hole with the first portion 511. The first connecting strap 561 and the second connecting strap 562 are detachably connected, thereby facilitating the upper arm of the detection object 700 to pass through the wearing hole, and improving the convenience of wearing this RF coil assembly.

In some embodiments, the first connecting strap 561 is bonded to the second connecting strap 562 via the Velcro. For example, one of the first connecting strap 561 and the second connecting strap 562 is an elastic strap, and the other of the first connecting strap 561 and the second connecting strap 562 is provided with the Velcro 550. The first connecting strap 561 and the second connecting strap 562 are bonded with each other via the Velcro 550. In some embodiments, expansion and contraction of the third connecting mechanism 560 may be achieved by a change in the position in which the Velcro 550 is bonded.

In some embodiments, as shown in FIG. 5 and FIG. 7, the first layer 510 may be curved. Specifically, both the first portion 511 and the second portion 512 are curved, which facilitates adapting with the acromion region and the upper arm region of the shoulder of the detection object 700, so that the first layer 510 more closely fits the shoulder of the detection object 700.

In some embodiments, as shown in FIG. 5 and FIG. 6, the second layers 520 may be planar shaped, which facilitates adaptation to the chest region or the scapular region of the detection object 700, allowing for a better fit to the shoulder of the detection object 700.

In some embodiments, as shown in FIG. 5, the region of the first layer 510 disposed between the two second layers 520 has an arcuate notch 513 for avoiding the neck of the detection object 700 so that the RF coil assembly more closely fits the shoulder of the detection object 700.

In some embodiments, as shown in FIG. 5, an end of the first portion 511 proximate to the second layer 520 may be arcuate to fit to the root of the upper arm of the detection object 300.

In some embodiments, the wearable RF coil assembly in FIG. 5-FIG. 8 may be used for body parts other than the shoulder, e.g., the chest, the back, or the like. Taking the detection site as the chest as an example, the first connecting strap 561 and the second connecting strap 562 may be connected around the armpit of the detection object 700, and the first layer 510 and the second layers 520 are unfolded into a flat surface as shown in FIG. 5. The first layer 510 and the second layer 520 are attached to the chest of the detection object 700.

In some embodiments, when a wearable structure formed by the wearable RF coil assembly (e.g., the wearable RF coil assembly 400) is worn, the wearable structure is in the shape of a tube, the detection site is the head, elbow, shoulder, knee, ankle, abdomen, or chest, etc. The following takes the wearable RF coil assembly shown in FIGS. 9-12 as an example to describe the wearable RF coil assembly in the shape of a tube. The wearable RF coil assembly in FIG. 9-FIG. 12 includes flexible cladding layers 900 and malleable conductors 1000.

Figure 9:
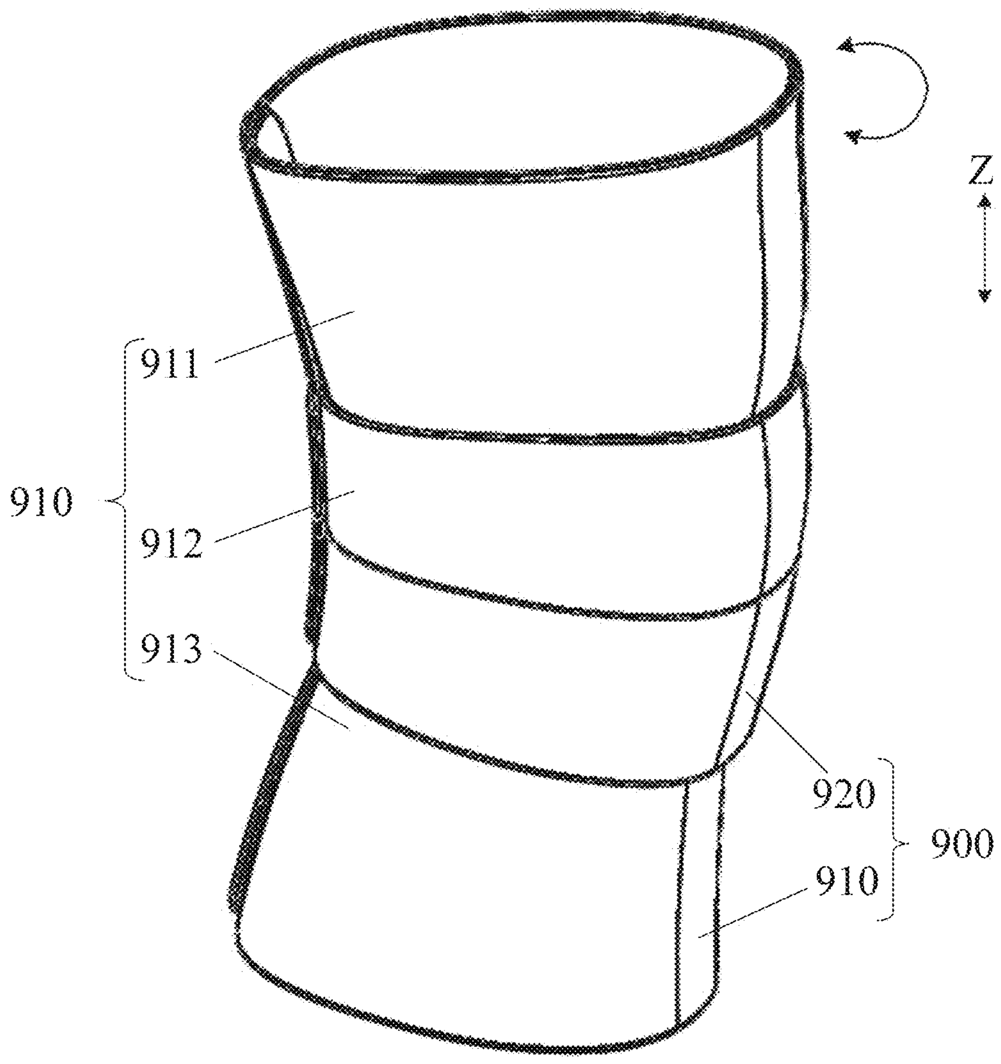
FIG. 9 is a schematic diagram illustrating an exemplary wearable structure formed by a wearable RF coil assembly according to some embodiments of the present disclosure.

FIG. 9 is a schematic diagram illustrating an exemplary wearable structure formed by a wearable RF coil assembly according to some embodiments of the present disclosure. As shown in FIG. 9, the wearable RF coil assembly includes flexible cladding layers 900, and the wearable structure formed by the RF coil assembly is in the shape of a tube when worn. A circumferential direction of the flexible cladding layers 900 is the direction shown by the helix line in FIG. 9, and an axial direction of the flexible cladding layers 900 is the direction Z in FIG. 9.

Figure 10:
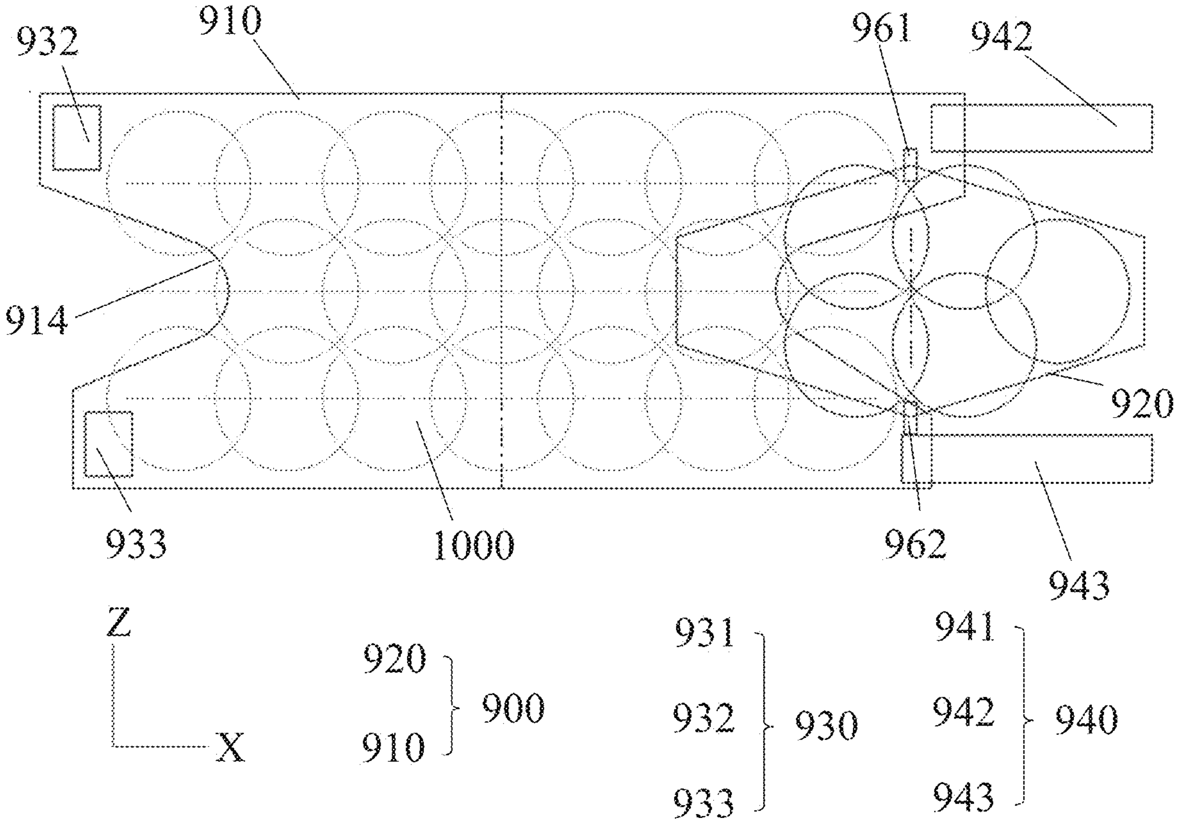
FIG. 10 is a schematic diagram illustrating the wearable RF coil assembly in FIG. 9 when unfolded.
Figure 11:
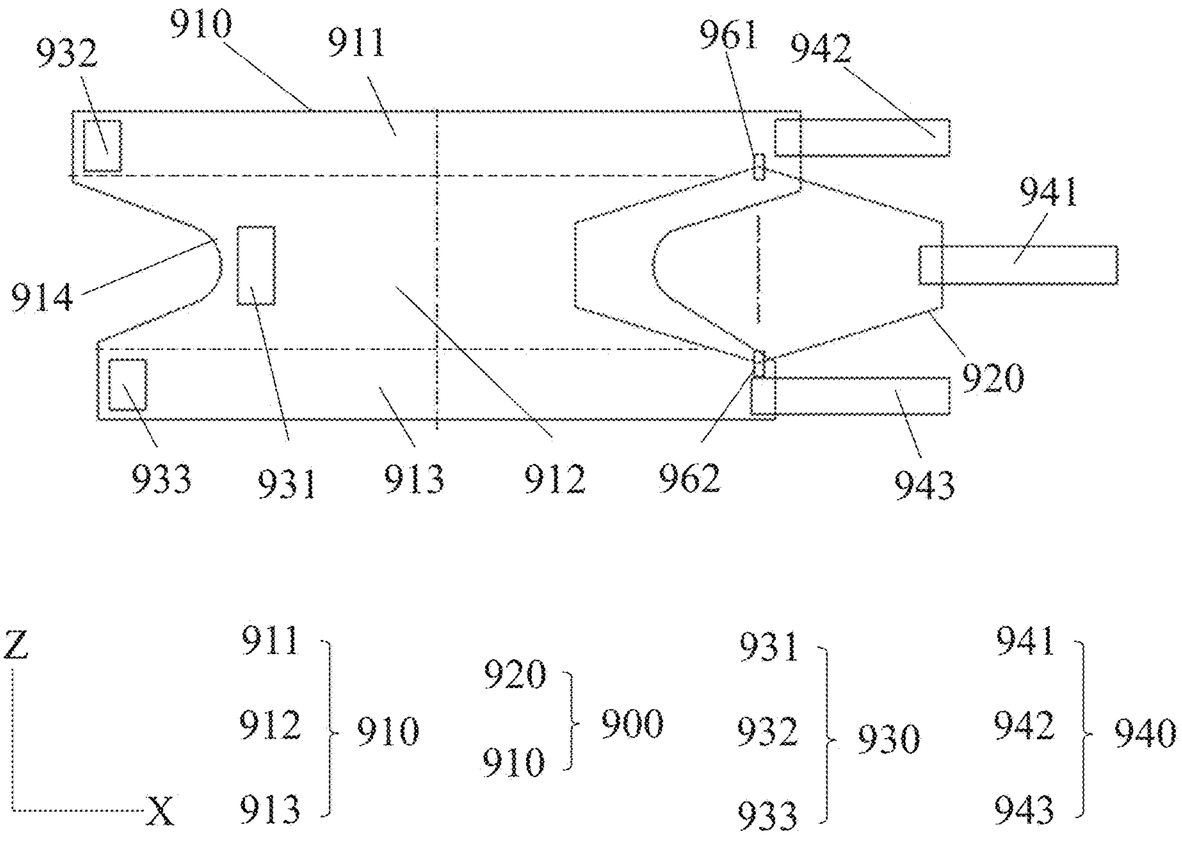
FIG. 11 is a schematic diagram illustrating a flexible cladding layer in the wearable RF coil assembly in FIG. 9.

The following part of the present disclosure takes that the detection site is the knee as an example to describe, and in this case, the wearable RF coil assembly is a wearable coil assembly of the knee. FIG. 10 and FIG. 11 show the wearable RF coil assembly in FIG. 9 when in a deployed state. The circumferential direction of the flexible cladding layers 900 is the direction X in FIG. 10 and FIG. 11, and the axial direction of the flexible cladding layers 900 is the direction Z in FIG. 10 and FIG. 11. As shown in FIG. 10 and FIG. 11, the flexible cladding layers 900 are provided with a plurality of connecting components along the circumferential direction, and these connecting components include a first connecting unit 930 and a second connecting unit 940. The first connecting unit 930 is capable of being detachably connected to different positions of the second connecting unit 940 to adjust the circumferential dimension of a detection space enclosed by the flexible cladding layers 900 along the circumferential direction. As shown in FIG. 10, the plurality of malleable conductors 1000 form a plurality of RF coils that are disposed within the flexible cladding layers 900.

In the wearable RF coil assembly shown in FIGS. 9-12, the first connecting unit 930 is connected to different positions of the second connecting unit 940, such that the circumferential dimension of the detection space enclosed by the flexible cladding layers 900 is changed. Therefore, the wearable RF coil assembly may adapt to different detection sites of detection objects with different body sizes, reducing the gap between the wearable structure formed by the RF coil assembly and the detection site, making the wearable structure fit the detection site better, solving the problem of non-fit caused by the size difference and the shape difference of the different detection sites of the different detection objects, and thus improving the quality of the scanning imaging. Additionally, the wearable RF coil assembly can be worn to the corresponding detection site by the detection object himself/herself, and after entering the scanning room of the magnetic resonance device, the detection object only needs to lie down on the scanning bed of the magnetic resonance device, and then connect the cable of the wearable RF coil assembly to the scanning bed of the magnetic resonance device, which greatly reduces the complexity of the workflow, saves time, and improves the scanning efficiency.

The flexible covering layers 900 may be made of a flexible material such as felt or PU using a hot pressing or sewing process, so as to make the wearable RF coil assembly flexible and capable of unfolding into a planar structure for wearing by the detection object. After being worn, the flexible wrapping layers 900 may be coiled into a structure in the shape of a tube for a better fit with the detection site. A plurality of RF coils formed by the plurality of malleable conductors 1000 are set up in an array and adjacent RF coils overlap with each other for decoupling, which reduces the signal-to-noise ratio. The malleable conductors 1000 are made of a flexible material, which further improves the softness of the wearable RF coil assembly, facilitates the wrapping of the wearable RF coil assembly around the detection site or the unfolding of the wearable RF coil assembly, thereby ensuring the imaging effect of the detection site while improving the wearing comfort.

In some embodiments, as shown in FIG. 11, the first connecting unit 930 may include a first connecting sub-portion 931, the second connecting unit 940 includes a first connecting mother portion 941, and the flexible cladding layers 900 include a main layer 910 and an accessory layer 920. The accessory layer 920 may be configured to wrap the patella region of the detection object. The first connecting sub-portion 931 is disposed on the main layer 910, the first connecting mother portion 941 is disposed on the accessory layer 920, and the first connecting sub-portion 931 may be capable of being detachably connected to different positions of the first connecting mother portion 941. By changing the connection position between the first connecting mother portion 941 and the first connecting sub-portion 931, the size of the detection space enclosed by the wearable RF coil assembly may be adjusted to adapt to the detection site of the detection object.

Merely by way of example, as shown in FIG. 11, when the detection object is thin, the first connecting sub-portion 931 may be connected to an end of the first connecting mother portion 941 close to the accessory layer 920, so that the detection space decreases. When the detection object is fat, the first connecting sub-portion 931 may be connected to an end of the first connecting mother portion 941 away from the accessory layer 920, so that the detection space increases. The first connecting sub-portion 931 may be a sub-Velcro, the first connecting mother portion 941 may be a mother Velcro, and the area of the first connecting mother portion 941 is larger than the area of the first connecting sub-portion 931, which is convenient for adjusting the connection position between the first connecting sub-portion 931 and the first connecting mother portion 941. In some embodiments, the first connecting sub-portion 931 and the first connecting mother portion 941 may be other structures with adjustable length, which may be fixed or detachable. For example, the first connecting sub-portion 931 and the first connecting mother portion 941 may be fixed elastic straps. As another example, the first connecting sub-portion 931 and the first connecting mother portion 941 may be detachable clastic straps or snap structures.

In some embodiments, as shown in FIG. 10 and FIG. 11, the main layer 910 and the accessory layer 920 may have an overlapping region, and the accessory layer 920 may be capable of being connected to different positions of the main layer 910 to adjust the area of the overlapping region. By changing the connection position of the accessory layer 920 and the main layer 910 to adjust the area of the overlapping region, and accordingly, change the protrusion area of the accessory layer 920 with respect to the main layer 910, and further change the size of the detection space enclosed by the wearable RF coil assembly, thereby better adapting to the difference in size of the detection sites of different detection objects.

In some embodiments, as shown in FIGS. 10 and 11, the accessory layer 920 is capable of being moved along the circumferential direction to enable an end of the accessory layer 920 along a direction (e.g., axial direction) perpendicular to the circumferential direction to be capable of being detachably connected to different positions of the main layer 910, thereby changing the area of the overlapping region of the accessory layer 920 and the main layer 910.

In some embodiments, the first connecting mother portion 941 may be provided at an end of the accessory layer 920 along the circumferential direction, and the other end of the accessory layer 920 along the circumferential direction may be fixedly connected to the main layer 910. By fixing one end of the accessory layer 920 to the main layer 910, the possibility of offsetting when the accessory layer 920 is adjusted is reduced, and the reliability of adjusting the connection position of the accessory layer 920 and the main layer 910 is improved.

In some embodiments, as illustrated in FIG. 10 and FIG. 11, the accessory layer 920 may be movable in an axial direction with respect to the main layer 910, and two ends of the accessory layer 920 are connected to the main layer 910 by a first connecting member 961 and a second connecting member 962, respectively. Merely by way of example, the first connecting member 961 and the second connecting member 962 may be elastic bands, and the clastic bands may be fixed or detachable. The connection position between the accessory layer 920 and the main layer 910 may be changed by stretching or contracting the clastic bands, thereby changing the size of the detection space. In some embodiments, the first connecting member 961 and the second connecting member 962 may be other structures with adjustable lengths, which may be fixed or detachable. For example, the first connecting member 961 and the second connecting member 962 may be removable Velcro structures or snap structures, etc.

Figure 12:
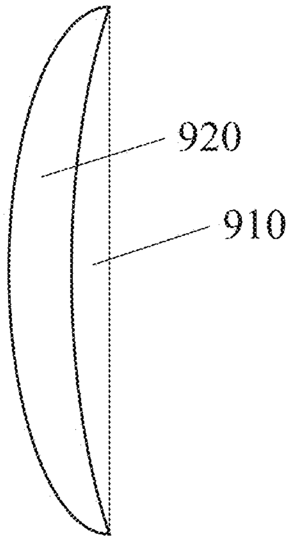
FIG. 12 is a side view of the flexible cladding layer in the wearable RF coil assembly in FIG. 9.

In some embodiments, as illustrated in FIG. 9 and FIG. 12, the accessory layer 920 may be convex in a direction away from the plurality of RF coils, and the main layer 910 may be concave in a direction away from the plurality of RF coils. Since the plurality of RF coils are formed by the malleable conductors 1000, the accessory layer 920 may be regarded to be convex in a direction away from the malleable conductors 1000, and the main layer 910 may be regarded to be concave in a direction away from the malleable conductors 1000. In this way, the accessory layer 920 may adapt to bumps at the joints (e.g., at the knee patella, at the elbow joint, etc.), and the main layer 910 may adapt to depressions at the joints (e.g., at the popliteal fossa of the knee, at the elbow joint, etc.), which enhances the fitting effect of the wearable RF coil assembly and the detection site.

In some embodiments, the curvature degree of the layer, i.e., at least one of the convex of the accessory layer 920 and the concave of the main layer 910, may be determined by a machine learning model. An input of the machine learning model is information of the detection object (e.g., age, gender, height, weight, etc.), the detection site of the detection object, etc., and an output of the machine learning model is the curvature degree of the layer (i.e., the curvature of the convex of the accessory layer 920 and/or the concave of the main layer 910).

In some embodiments, as shown in FIG. 10 and FIG. 11, a region where the main layer 910 is connected to the accessory layer 920 may be provided with a curved opening 914 such that the flexible cladding layers 900 may avoid a protruding patellar part after winding. Correspondingly, the shape of the accessory layer 920 may be hexagonal, such that after the accessory layer 920 is wound with the main layer 910, the accessory layer 920 may cover the curved opening 914.

In some embodiments, as shown in FIG. 11, the first connecting unit 930 may include a second connecting sub-portion 932, and the second connecting unit 940 may include a second connecting mother portion 942. The main layer 910 may include a first sub-layer 911 and a second sub-layer 912 that are connected to each other and distributed in a direction (e.g., the axial direction) perpendicular to the circumferential direction. The first connecting sub-portion 931 is disposed in the second sub-layer 912. The second connecting sub-portion 932 and the second connecting mother portion 942 are respectively disposed at two ends of the first sub-layer 911 along the circumferential direction. The second connecting sub-portion 932 is capable of being detachably connected to different positions of the second connecting mother portion 942. By such a setting, the second sub-layer 912 may be adhered to the patella of the detection object, and the first sub-layer 911 may be adhered to the thigh of the detection object, to better accommodate the size differences between the detection sites of different detection objects, improving the tightness of the fit, thus improving the quality of the scanning image.

In some embodiments, as shown in FIG. 11, the first connecting unit 930 may include a third connecting sub-portion 933 spaced from the second connecting sub-portion 932, and the second connecting unit 940 may include a third connecting mother portion 942 spaced from the second connecting mother portion 943. The main layer 910 may include a third sub-layer 913 distributed in the direction perpendicular to the circumferential direction and connected to the second sub-layer 912. The third connecting sub-portion 933 and the third connecting mother portion 943 are respectively disposed at two ends of the third sub-layer 913 along the circumferential direction. The third connecting sub-portion 933 may be capable of being detachably connected to different positions of the third connecting mother portion 943. A dimension of the third sub-layer 913 along the circumferential direction is smaller than a dimension of the first sub-layer 911 along the circumferential direction. By such a setting, the difference between the thigh-side diameter and the calf-side diameter of the knee joint may be adapted to make the fit between the knee joint and the wearable RF coil assembly better.

In the embodiments of the present disclosure, the fit of the wearable RF coil assembly to the knee joint is greatly improved by setting the main layer 910 as a type with three segments connected in sequence to better match the size difference between the thigh side, the patella side, and the calf side, thus improving the quality of the scanning imaging.

In some embodiments, the first connecting sub-portion 931 and the first connecting mother portion 941, the second connecting sub-portion 932 and the second connecting mother portion 942, and the third connecting sub-portion 933 and the third connecting mother portion 943 are detachable structures such as a Velcro, a carabiner-type, a perforation-type structure, a tieable cord-type structure, or the like.

In some embodiments, the wearable RF coil assembly may include a plurality of malleable conductors (e.g., the malleable conductors 800 and the malleable conductors 1000) and a wearable structure. The plurality of malleable conductors form a plurality of RF coils of the magnetic resonance device.

In some embodiments, the wearable structure may be in a shape of a scapular, including an upper arm component (e.g., the first layer 510) and a shoulder component (e.g., the second layer 520) connected with each other. Both the upper arm component and the shoulder component include flexible cladding layers provided with the plurality of RF coils. The upper arm component surrounds the upper arm of the detection object (e.g., the detection object 700) and the shoulder component wraps around the front and back of the shoulder of the detection object. The flexible cladding layers include at least two layers that are capable of being moved relative to each other to allow the detection space of the wearable structure to be adapted to the shoulder of the detection object.

Merely by way of example, the wearable structure in the shape of a scapular may be a wearable structure formed by the wearable RF coil assembly in FIGS. 5-8. The flexible cladding layers 500 of the wearable structure may include three layers, namely a first layer 510 and two second layers 520. Two layers of these three layers (i.e., the two second layers 520) are respectively disposed on the left side and the right side of the other layer (i.e., the first layer 510) and have an overlapping region with the other layer, respectively. When the wearable structure wraps around the shoulder of the detection object, the three layers are capable of being moved relative to each other to enable the detection space of the wearable structure to be adapted to the shoulder of the detection object, so that the wearable structure may be well fitted to the shoulder, which improves the quality of the scanning imaging.

In some embodiments, the wearable structure may be in the shape of a scapular and include a main portion (e.g., the main layer 910) and an accessory portion (e.g., the accessory layer 920) connected with each other. Both the main portion and the accessory portion include flexible cladding layers provided with the plurality of RF coils formed by malleable conductors (e.g., the malleable conductors 1000). The main portion and the accessory portion have an overlapping region, and the accessory portion is connected to different positions of the main portion by a detachable structure to adjust the area of the overlapping region.

Merely by way of example, the above wearable structure in the shape of a scapular may be a wearable structure formed by the wearable RF coil assembly in FIGS. 9-12. The main portion (i.e., the main layer 910) may include a first sub-layer (i.e., the first sub-layer 911), a second sub-layer (i.e., the second sub-layer 912), and a third sub-layer (i.e., the third sub-layer 913) distributed along in the direction (e.g., the axial direction) perpendicular to the circumferential direction of the flexible cladding layers. The first sub-layer and the third sub-layer are connected to the second sub-layer, and a dimension of the third sub-layer along the circumferential direction is less than a dimension of the first sub-layer along the circumferential direction. With the above-described wearable structure, the detection space thereof may be well adapted to the dimensions of different detection sites (e.g., head, elbow, shoulder, knee, ankle, abdomen, or chest, etc.) of different detection objects, so that the wearable structure may fit the detection sites well, thereby improving the quality of the scanning imaging.

When scanning the detection object using MR, it is necessary for the detection object to remain motionless, otherwise motion artifacts may be generated. In order to minimize the motion of the detection site of the detection object, auxiliary accessories such as sandbags and mats are generally used to immobilize the detection object. When sandbags are used as the auxiliary accessory, the weight of the sandbags is utilized to fix the detection site of the detection object. Sandbags are usually designed in the shape of a flat bag filled with sand. However, with this design, if they are filled with more sand, sandbags are not easy to bend and weigh is heavy, and if the sandbags are filled with less sand, the sand tends to pile up at one end. Both of these cases are difficult to fit the detection site that needs to be fixed, and it is difficult to balance the fixation of the detection site and the comfort of the detection object.

In the embodiments of the present disclosure, by using a partitioned sandbag structure in the plurality of flexible cladding layers of the wearable RF coil assembly, the filling amount of sand is significantly reduced. The sandbag structure is easy to bend, and may be better adhered to the detection site, taking into account the fixation of the detection site and the comfort of the detection object. Additionally, a count of partitions of the sandbag structure may be adjusted according to the size of the detection site, which is flexible and may be well adapted to different detection sites.

In some embodiments, the interior of at least one of the plurality of flexible cladding layers may be a sandbag structure. The sandbag structure may include at least two partitions, neighboring partitions of the at least two partitions are divided by sutures, and each of the at least two partitions is filled with a filler. Merely by way of example, a flexible cladding layer 1300 shown in FIG. 13A and FIG. 13B, a flexible cladding layer 1400 shown in FIG. 14, a flexible cladding layer 1500 shown in FIG. 15A and FIG. 15B, all of which have a sandbag structure inside. In some embodiments, the flexible covering layers of the sandbag structure may be used to cover joints (e.g., knees, elbows, etc.) of the detection object to prevent movement.

Figure 13A:
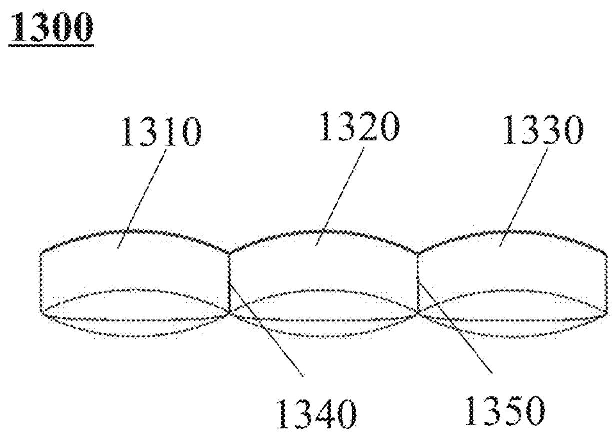
FIG. 13A and FIG. 13B are schematic diagrams illustrating an exemplary flexible cladding layer in a wearable RF coil assembly according to some embodiments of the present disclosure.
Figure 13B:
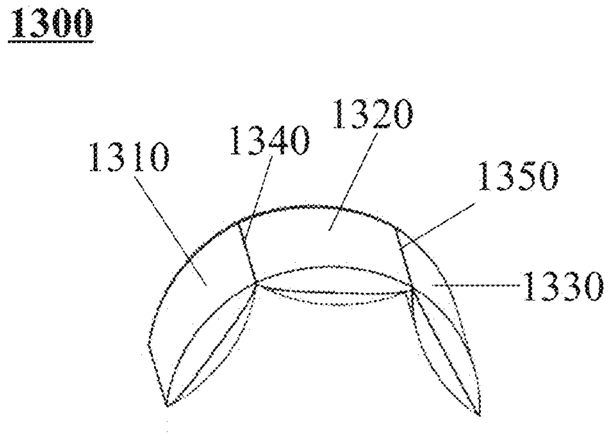
Figure 14A:
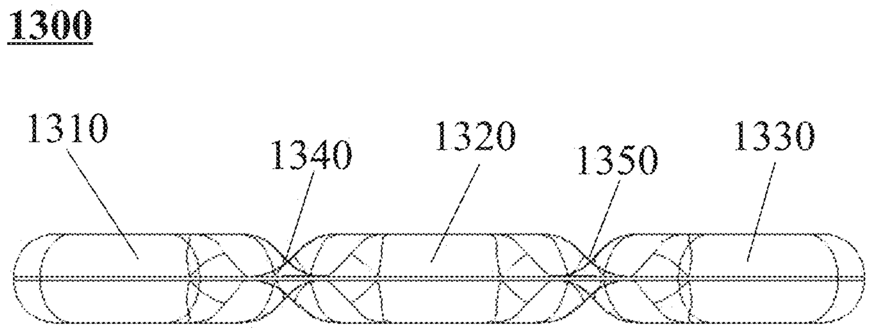
FIG. 14A and FIG. 14B are schematic diagrams illustrating the flexible cladding layers in FIG. 13A and FIG. 13B.
Figure 14B:
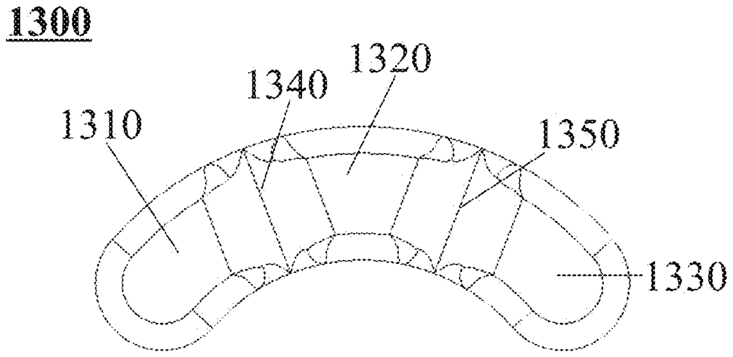

FIG. 13A and FIG. 13B are schematic diagrams illustrating an exemplary flexible cladding layer in a wearable RF coil assembly according to some embodiments of the present disclosure. FIG. 13A illustrates the state of the flexible cladding layer 1300 when unfolded, and FIG. 13B illustrates the state of the flexible cladding layer 1300 when bent (i.e., when worn). As shown in FIG. 13A and FIG. 13B, the interior of flexible cladding layer 1300 is the sandbag structure and includes three partitions, namely a partition 1310, a partition 1320, and a partition 1330. The partition 1310 and the partition 1320 are divided by sutures 1340, and the partition 1320 and the partition 1330 are divided by sutures 1350. FIG. 14A and FIG. 14B are schematic diagrams illustrating the flexible cladding layers in FIG. 13A and FIG. 13B. FIG. 14A corresponds to FIG. 13A, and FIG. 14B corresponds to FIG. 13B. As shown in FIGS. 14A and 14B, interiors of the partition 1310, the partition 1320, and the partition 1330 are all hollow structures, filled with a filler such as sand, water, gel, etc., and exteriors of the partition 1310, the partition 1320, and the partition 1330 may be sewn with materials such as cotton, linen, chemical fibers (e.g., PU, etc.), or the like.

Figure 15:
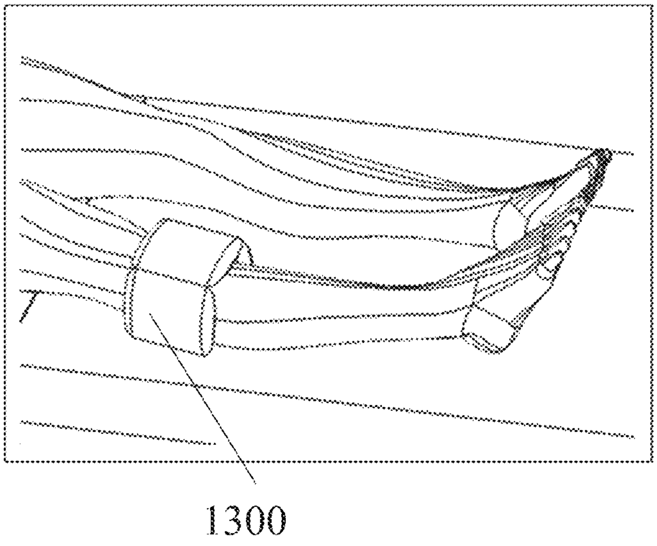
FIG. 15 is a schematic diagram illustrating that a detection object wears the wearable RF coil assemblies in FIG. 13A and FIG. 13B.

As shown in FIGS. 13B and 14B, the flexible cladding layer 1300, when bent, may form a semi-annular wearable structure that may adapt to joints (e.g., knees, elbows, etc.), or the like. Merely by way of example, as shown in FIG. 15, when the wearable RF coil assembly is used for the knee of the detection object, the flexible cladding layer 1300 in FIG. 13A and FIG. 13B, after bending, may well cover and wrap the knee of the detection object to achieve a good fit, taking into account the fixation of the detection site and the comfort of the detection object.

In some embodiments, the count of partitions in the sandbag structure may be determined based on the size of a covered site. The covered site is a site covered by the flexible cladding layers of the sandbag structure. The larger the size of the covered site, the greater the count of partitions may be. For example, the count of partitions may be 4 or 5 when the covered site is a knee, and the count of partitions may be 2 or 3 when the detection site is an elbow. By adjusting the count of partitions of the sandbag structure according to the size of the covered site, the usage flexibility is improved and the sandbag structure may be well adapted to different covered sites.

In some embodiments, the wearable RF coil assembly (e.g., the wearable RF coil assembly shown in FIGS. 5-8 and the wearable RF coil assembly shown in FIGS. 9-12) may further include an amplifier. The amplifier is connected to the plurality of RF coils in the wearable RF coil assembly by a wired connection or a wireless connection. The wired connection may include a cable connection, and the wireless connection may include a WiFi connection, a Bluetooth connection, etc. By connecting the amplifier to the RF coils in the wearable RF coil assembly in the wired connection or the wireless connection, the convenience of connecting the RF coil assembly to the magnetic resonance device is improved (e.g., the wireless connection requires only that the detection object wear the RF coil assembly and then enter the scanning room of the magnetic resonance device and lie down on the scanning bed of the magnetic resonance device), the complexity of the workflow is greatly reduced and time is saved, and the requirement for the detection object's cooperation is greatly reduced, thus improving the scanning efficiency. By setting the amplifier on the outside of the wearable structure, the wearable structure is made thinner and lighter, which improves the wearing comfort and fits the detection site better.

In some embodiments, when the wireless connection is used, the wearable RF coil assembly includes a wireless signal transmitting component, an amplifier, and a wireless signal receiving component. The amplifier and the wireless signal receiving component may be connected to each other and placed in the scanning bed of the magnetic resonance device, and the wireless signal transmitting component is placed in the flexible cladding layer and connected to the RF coils, which avoids the effect of the amplifier being placed in the RF coils on the flexibility of the coils, and the wireless signal transmitting component is small enough to have a limited effect on the flexibility of the coil.

In some embodiments, the wearable RF coil assembly may include a flexible connecting wire, and the amplifier may be electrically connected to the plurality of RF coil units via the flexible connecting wire.

Figure 16A:
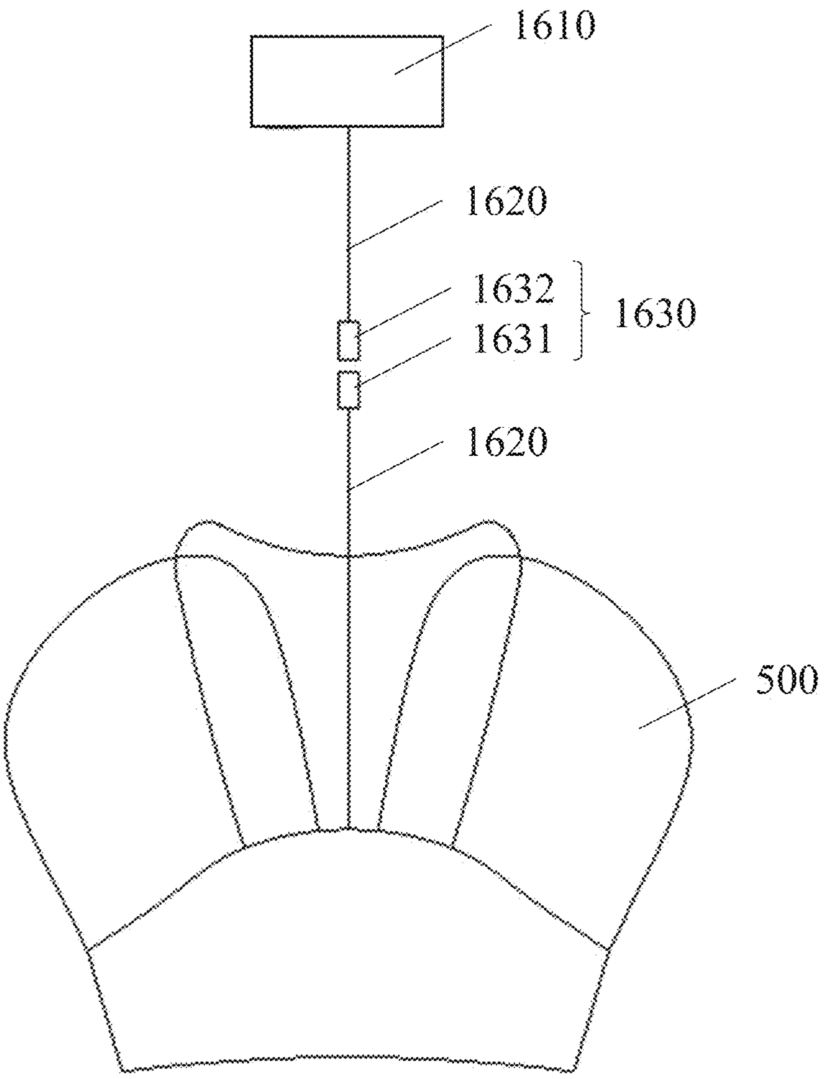
FIG. 16A is a schematic diagram illustrating a connection between an amplifier and the RF coils in the wearable RF coil assembly in FIG. 5.
Figure 16B:
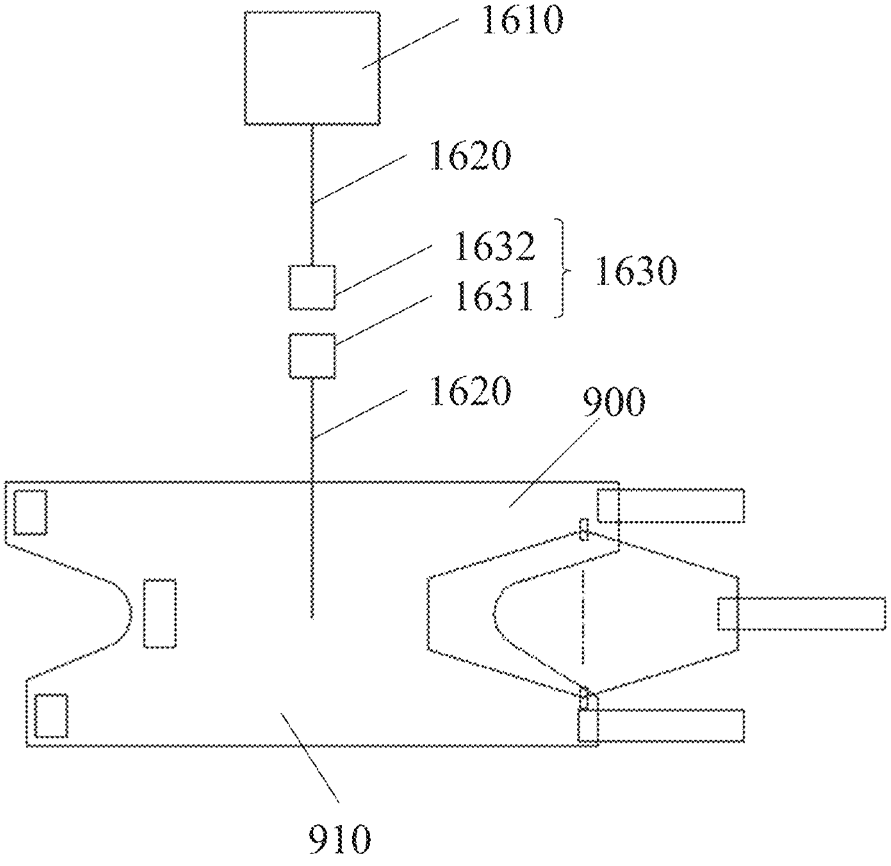
FIG. 16B is a schematic diagram illustrating a connection between an amplifier and RF coils in the wearable RF coil assembly in FIG. 11.

Merely by way of example, FIG. 16A is a schematic diagram illustrating a connection between an amplifier and the RF coils in the wearable RF coil assembly in FIG. 5, and FIG. 16B is a schematic diagram illustrating a connection between an amplifier and RF coils in the wearable RF coil assembly in FIG. 11. As shown in FIG. 16A and FIG. 16B, the wearable RF coil assemblies of FIG. 5 and FIG. 11 may include an amplifier 1610 and a flexible connecting line 1620. The amplifier 1610 is electrically connected to the RF coils formed by the malleable conductors via the flexible connecting wire 1620. Further, as shown in FIG. 16A, the amplifier 1610 is electrically connected to the malleable conductors 800 within the first portion 511 via the flexible connecting wire 1620. As shown in FIG. 16B, the amplifier 1610 is electrically connected to the malleable conductors 1000 within the main layer 910 via the flexible connecting wire 1620. The wearable RF coil assembly further includes a connector 1630, the connector 1630 including a first connecting portion 1631 and a second connecting portion 1632. The malleable conductors are electrically connected to the first connecting portion 1631 via the flexible connecting wire 1620, and the amplifier 1610 is electrically connected to the second connecting portion 1632 via the flexible connecting wire 1620. The first connecting portion 1631 is detachably connected with the second connecting portion 1632, thereby electrically connecting and disconnecting the amplifier 1610 from the wearable RF coil assembly. Preferably, the connection between the first connecting portion 1631 and the second connecting portion 1632 is a plug fit.

In some embodiments, the amplifier may be placed inside the wearable RF coil assembly. When the amplifier is placed inside the wearable RF coil assembly, the signal that has been amplified by the amplifier may be transmitted to the magnetic resonance device (e.g., the imaging device 110) via a wired connection or a wireless connection. The wired connection may include a cable connection, and the wireless connection may include a WiFi connection, a Bluetooth connection, or the like. When the connection is the wireless connection, the wearable RF coil assembly may further include a wireless signal sending component and a wireless signal receiving component. The wireless signal sending component is in a wired connection with the amplifier, and the wireless signal receiving component is disposed on a side of the magnetic resonance device. In this way, the amplifier is placed inside the wearable RF coil assembly, which improves the signal amplification performance, ensures the strength and reliability of the signal transmission, and thus improves the quality of the scanning.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" may mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python, or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. A wearable radio frequency (RF) coil assembly for a magnetic resonance device, comprising:
- a plurality of malleable conductors forming a plurality of RF coils of the magnetic resonance device; and
- a plurality of flexible cladding layers, wherein at least two of the plurality of flexible cladding layers have an overlapping region, the overlapping region is capable of being adjusted, and the plurality of RF coils are disposed within the plurality of flexible cladding layers, wherein
  - each of the plurality of flexible cladding layers is provided with a plurality of connecting components,
  - the plurality of flexible cladding layers are connected to each other by the plurality of connecting components to enable the wearable RF coil assembly to form a wearable structure, and
  - the wearable structure adapts to detection sites of various sizes or shapes, and when the wearable structure is worn by a detection object, an inner surface of the wearable structure adheres to a detection site of the detection object.

2. The wearable RF coil assembly of claim 1, wherein when the wearable structure is worn, the wearable structure is in a shape of a tube, a helmet, a boot, or a scapula.

3. The wearable RF coil assembly of claim 2, wherein when the wearable structure is worn, the wearable structure is in the shape of the scapular, the detection site is a shoulder, and the plurality of flexible cladding layers include a first layer and two second layers, the two second layers are respectively provided on a left side and a right side of the first layer, and partially overlap with the first layer respectively; and when the plurality of flexible cladding layers wrap the shoulder, the two second layers are capable of being moved relative to the first layer to allow a detection space of the wearable structure to adapt to the shoulder.

4. The wearable RF coil assembly of claim 3, wherein the plurality of connecting components include a first connecting mechanism, one end of the first connecting mechanism is connected to one of the two second layers and the other end of the first connecting mechanism is connected to the other of the two second layers or the first layer.

5. The wearable RF coil assembly of claim 4, wherein the plurality of connecting components further include a second connecting mechanism, one end of the second connecting mechanism is connected to one of the two second layers and the other end of the second connecting mechanism is connected to the other of the two second layers, and the second connecting mechanism is configured to be fitted onto the detection object and tension the two second layers.

6. The wearable RF coil assembly of claim 3, wherein the first layer includes a first portion and a second portion, the two second layers and the second portion are connected to the first portion, the two second layers are respectively located on two sides of the first portion and partially overlap with the second portion respectively, the two second layers are capable of being moved relative to the second portion.

7. The wearable RF coil assembly of claim 6, wherein the plurality of connecting components further include a third connecting mechanism, two ends of the third connecting mechanism are respectively connected to two opposite ends of the first portion, and the third connecting mechanism and the first portion enclose a hole for an upper arm of the detection object to pass through, and a length of the third connecting mechanism is capable of being adjusted.

8. The wearable RF coil assembly of claim 3, wherein a region, disposed between the two second layers, of the first layer has an arcuate notch for avoiding a neck of the detection object.

9. The wearable RF coil assembly of claim 2, wherein when the wearable structure is worn, the wearable structure is in the shape of the tube, the plurality of connecting components are provided along a circumferential direction of the plurality of flexible cladding layers, the plurality of connecting components includes a first connecting unit and a second connecting unit, the first connecting unit is capable of being detachably connected to different positions of the second connecting unit to adjust a circumferential dimension of a detection space enclosed by the plurality of flexible cladding layers along the circumferential direction of the plurality of flexible cladding layers.

10. The wearable RF coil assembly of claim 9, wherein the first connecting unit includes a first connecting sub-portion and the second connecting unit includes a first connecting mother portion, and the plurality of flexible cladding layers include a main layer and an accessory layer, the first connecting sub-portion is disposed on the main layer, the first connecting mother portion is disposed on the accessory layer, and the first connecting sub-portion is capable of being detachably connected to different positions of the first connecting mother portion.

11. The wearable RF coil assembly of claim 10, wherein the main layer and the accessory layer have an overlapping region and the accessory layer is capable of being connected to different positions of the main layer to adjust an area of the overlapping region, the accessory layer is capable of being moved in the circumferential direction to enable an end of the accessory layer along a direction perpendicular to the circumferential direction to be capable of being detachably connected to the different positions of the main layer, or the first connecting mother portion is provided at the end of the accessory layer along the circumferential direction, and the other end of the accessory layer along the circumferential direction is fixedly connected to the main layer.

12. The wearable RF coil assembly of claim 10, wherein the accessory layer is convex in a direction away from the plurality of RF coils, and the main layer is concave in a direction away from the plurality of RF coils.

13. The wearable RF coil assembly of claim 10, wherein the first connecting unit includes a second connecting sub-portion and the second connecting unit includes a second connecting mother portion, and the main layer includes a first sub-layer and a second sub-layer connected to each other and distributed in a direction perpendicular to the circumferential direction, the first connecting sub-portion is disposed in the second sub-layer, the second connecting sub-portion and the second connecting mother portion are respectively disposed at two ends of the first sub-layer along the circumferential direction, and the second connecting sub-portion is capable of being detachably connected to different positions of the second connecting mother portion.

14. The wearable RF coil assembly of claim 13, wherein the first connecting unit includes a third connecting sub-portion spaced from the second connecting sub-portion, and the second connecting unit includes a third connecting mother portion spaced from the second connecting mother portion, and the main layer further includes a third sub-layer distributed in the direction perpendicular to the circumferential direction and connected to the second sub-layer, the third connecting sub-portion and the third connecting mother portion are respectively disposed at two ends of the third sub-layer along the circumferential direction, the third connecting sub-portion is capable of being detachably connected to different positions of the third connecting mother portion, and a dimension of the third sub-layer along the circumferential direction is smaller than a dimension of the first sub-layer along the circumferential direction.

15. The wearable RF coil assembly of claim 1, wherein an interior of at least one of the plurality of flexible cladding layers is a sandbag structure, the sandbag structure includes at least two partitions, neighboring partitions of the at least two partitions are divided by sutures, and each of the at least two partitions is filled with a filler.

16. The wearable RF coil assembly of claim 1, further comprising an amplifier connected to the plurality of the RF coils by a wired connection or a wireless connection.

17. A wearable RF coil assembly for a magnetic resonance device, comprising:

a plurality of malleable conductors forming a plurality of RF coils of the magnetic resonance device; and a wearable structure, wherein the wearable structure includes an upper arm portion and a shoulder portion connected with each other, both the upper arm portion and the shoulder portion include flexible cladding layers provided with the plurality of RF coils, the upper arm portion surrounds an upper arm of a detection object, the shoulder portion wraps around front and back of a shoulder of the detection object, the flexible cladding layers include at least two layers, and the at least two layers are capable of being moved relative to each other to allow a detection space of the wearable structure to be adapted to the shoulder of the detection object.

18. The wearable RF coil assembly of claim 17, wherein the flexible cladding layers of the wearable structure includes three layers, two layers of the three layers are respectively disposed on a left side and a right side of the other layer of the three layers and have an overlapping region with the other layer respectively, when the wearable structure wraps the shoulder of the detection object, the three layers are capable of being moved relative to each other to enable the detection space of the wearable structure to be adapted to the shoulder of the detection object.

19. A wearable RF coil assembly for a magnetic resonance device, comprising:

a plurality of malleable conductors forming a plurality of RF coils of the magnetic resonance device; and a wearable structure, wherein the wearable structure includes a main portion and an accessory portion connected with each other, both the main portion and the accessory portion include flexible cladding layers provided with the plurality of RF coils, the main portion and the accessory portion have an overlapping region, and the accessory portion is connected to different positions of the main portion by a detachable structure to adjust an area of the overlapping region.

20. The wearable RF coil assembly of claim 19, wherein the main portion includes a first sub-layer, a second sub-layer, and a third sub-layer distributed in a direction perpendicular to a circumferential direction of the flexible cladding layers, the first sub-layer and the third sub-layer are connected to the second sub-layer, a dimension of the third sub-layer along the circumferential direction is smaller than a dimension of the first sub-layer along the circumferential direction.

* * * * *